514-214
5/5/87 OR 000,271

United States Statutory Invention Registration [19]

[11] Reg. Number: H271

Whaun [43] Published: May 5, 1987

[54] TREATMENT OF MALARIA WITH ESTERS OF CEPHALOTAXINE

[75] Inventor: June M. Whaun, Rockville, Md.

[73] Assignee: The United States of America as represented by the Secretary of the Army, Washington, D.C.

[21] Appl. No.: 819,130

[22] Filed: Dec. 18, 1985

Related U.S. Application Data

[63] Continuation-in-part of Ser. No. 638,082, Aug. 6, 1984, abandoned.

[51] Int. Cl.[4] ..... A61K 31/55
[52] U.S. Cl. ..... 514/214
[58] Field of Search ..... 514/214

[56] References Cited

U.S. PATENT DOCUMENTS

| | | | |
|---|---|---|---|
| 3,870,727 | 3/1975 | Powell et al. | 260/326.5 |
| 3,959,312 | 5/1976 | Mikolajczak et al. | 260/326.29 |
| 4,203,996 | 5/1980 | Mikolajczak et al. | 424/274 |

OTHER PUBLICATIONS

Homoharringtonine NSC 141633, published by Investigational Drug Branch Cancer Therapy Evaluation Program Division of Cancer Treatment National Cancer Institute, Bethesda, Maryland, Jul. 1, 1981, revised Aug. 1982.

Coonley et al., Cancer Treatment Reports, vol. 67, pp. 693–696 (1983).

Warrell et al., Journal of Clinical Oncology, vol. 3, pp. 617–621 (1985) by American Society of Clinical Oncology.

*Primary Examiner*—John F. Terapane
*Assistant Examiner*—J. E. Thomas
*Attorney, Agent, or Firm*—Peter A. Taucher; Damian Porcari

[57] ABSTRACT

A method of treating animals for the control of malaria using the esters of cephalotaxine—harringtonine, homoharringtonine and deoxyharringtonine.

9 Claims, 2 Drawing Figures

Figure 1:
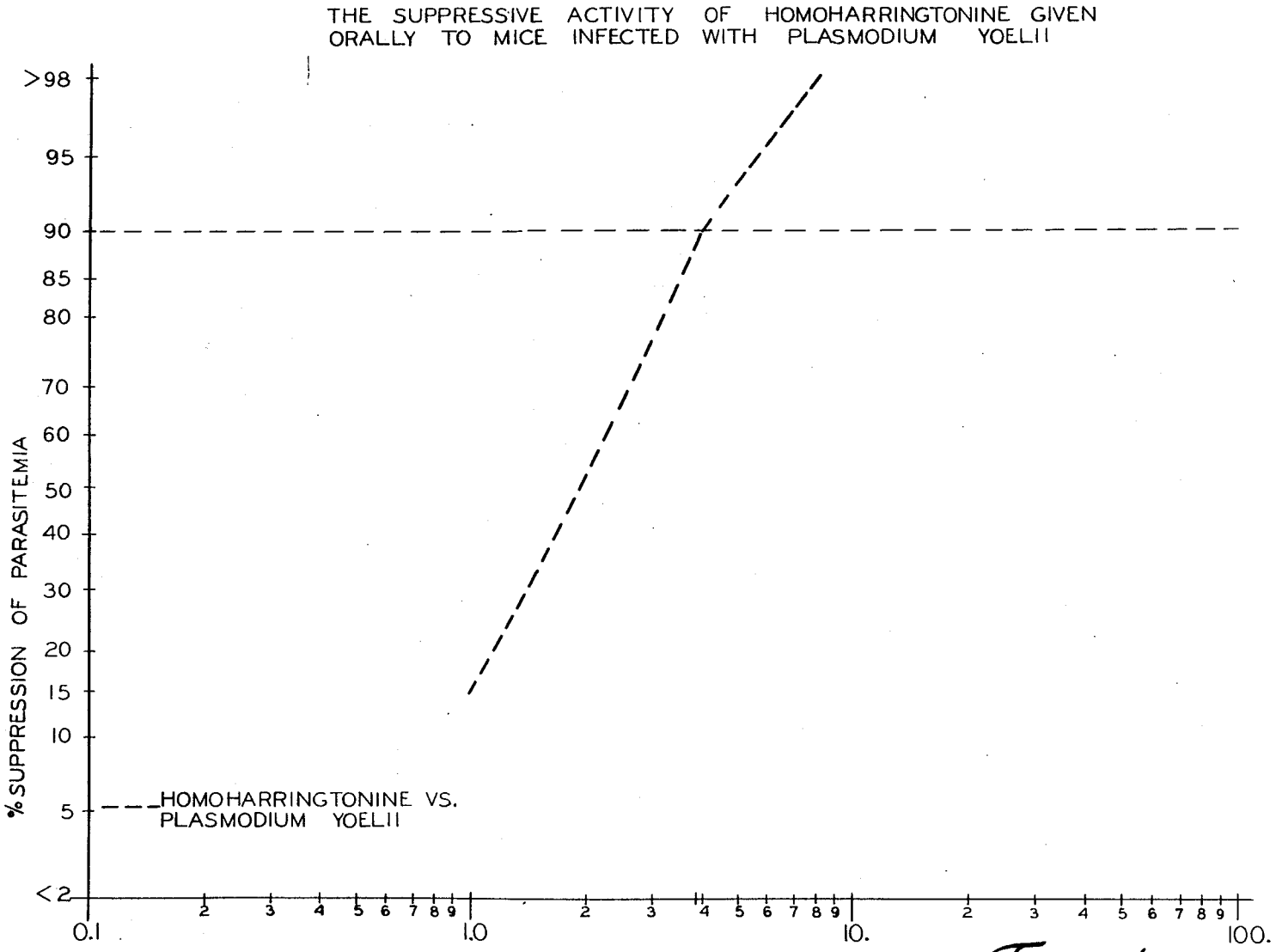

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

TREATMENT OF MALARIA WITH ESTERS OF CEPHALOTAXINE

GOVERNMENT INTEREST

The invention described herein may be manufactured, used, and licensed by or for the Government for governmental purposes without payment to me of royalty thereon.

This is a continuation-in-part of application Ser. No. 638,082 filed on Aug. 6, 1984, abandoned.

This invention deals with a novel use of harringtonine, homoharringtonine and deoxyhomoharringtonine for treating malaria.

Malaria has become an increasing problem in the tropical zones with the advent of chloroquine resistant strains of malaria parasites coupled with a decreased effectiveness of long acting insecticides such as DDT. The magnitude of the problem is reflected in the fact that malaria is the largest infectious disease in the world. Of the one billion people residing in malaria endemia areas, approximately 25 to 200 million people are diseased at any given time. In Africa alone, over one million children die each year from malaria.

The problem is becoming more serious as more stains of malaria become resistant to the major anti-malaria drug chloroquine. The major human pathogen is *Plasmodium falciparum.* More and more chloroquine resistant strains of *Plasmodium falciparum* have emerged in Central and South America, Africa, and Southeast Asia.

Researchers have synthesised chemical variants of chloroquine to combat new resistant malaria strains, however, these strains have already become resistant to the new drugs. A totally new drug having chemical properties different from chloroquine is needed to stem the increasing epidemic of resistant malaria strains.

While studying the biological processes of malaria parasite-infected cells, I noticed a resemblance to tumor cells. Both tumor cells and parasite-infected cells exhibit exponetial growth rates independent of the host. From this observation, I began testing antitumor drugs for their effectiveness as antimalarials. The most promising antitumor drugs are the esters of cephalotaxine—harringtonine, homoharringtonine and deoxyharringtonine. Synthesis of these compounds is described in U.S. Pat. Nos. 3,870,227 and 3,959,312.

Homoharringtonine is derived from a well-known Chinese herb used for many years in Fujian, China as a folk medicine for cancer. It is one group of cephalotoxus, yew-like evergreen coniferous trees, widely distributed in southern and northeastern China. Homoharringtonine, a white powder insoluble in water but soluble in alcohol, is a large heterocyclic molecule with a molecular weight of 545.6. The structures of harringtonine, homoharringtonine, and deoxyharringtonine are shown below:

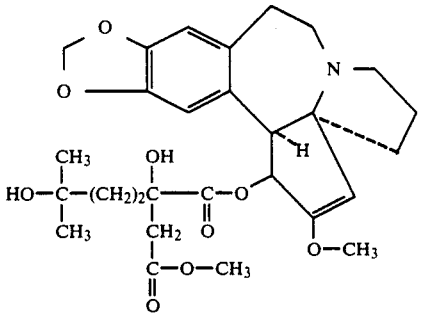

HARRINGTONINE

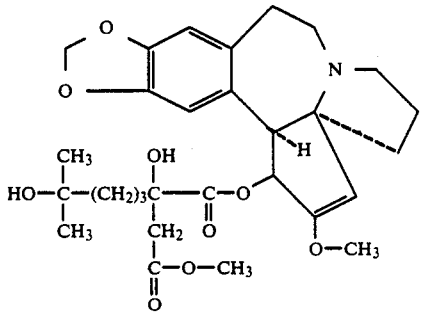

HOMOHARRINGTONINE

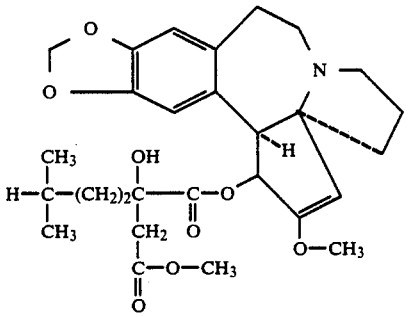

DEOXYHARRINGTONINE

Harringtonine and homoharringtonine have been tested by the National Cancer Instiute and the results of those studies published in a clinical brochure titled "Homoharringtonine" NSC 141633, published by Investigational Drug Branch Cancer Therapy Evaluation Program Division of Cancer Treatment National Cancer Institute Bethesda, Md. July 1, 1981, revised August 1982. The brochure reports of 3 Chinese clinical studies and an Australian use of cephalotoxus alkaloid drugs for the treatment of leukemia. The doses of harringtonine used in the Chinese studies range from 0.15–0.3 mg/kg per day for 5 to 10 days repeated every 7 to 14 days. The method of administration was not reported. Doses of homoharringtonine were 0.05–0.1 mg/kg administered using the same regimine. Mixtures of 1:3 and 2:1 harringtonine to homoharringtonine were also tested. The 1:3 mixture was administered in doses of 2 mg intramuscular, and 4 mg intravenous and the 2:1 mixture was administered in doses of 4 mg intravenous. Both mixtures were given daily for an unspecified number of days. The Chinese reported these dosages to be safe; producing mild side effects which abated when the drug was stopped.

Researchers in the U.S. studied the possibility of administering homoharringtonine as a continuous infusion to avoid acute autonomic toxicity. The primary side effect from homoharringtonine is hypotension. Hypotension is dose related and blood pressure returns to normal after treatment ends. See Coonley, et al., Cancer Treat Rep 67:693–696, 1983 and Warrell et al., J. Clin On col 3:617–621. Warrell et al. concluded that dose levels up to 5 mg/m$^2$ per day administered by continuous infusion for 9 days was safe and effective for acute nonlymphoelastic leukemia. Patients exhibited alopecia, diarrhea, hyperglycemia, and some weight gain in addition to hypotension. All side effects subsided after treatment stopped. The studies recommend continuous infusion of the drug to reduce the drugs toxic effects.

Homoharringtonine was tested in vitro and in vivo to determine its effectiveness against chloroquine-resistant strains of malaria parasites. Both in vivo and in vitro tests showed significant antimalarial activity. Applicant tested homoharringtonine in an in vitro malaria-infected red cell system. In this system, one parasite multiplies to 20 within 48 hours when left untreated. The dose required to cause 50% inhibition of parasite growth in 48 hours is called $ED_{50}$. A comparison of the $ED_{50}$ of homoharringtonine and chloroquine for 3 strains for malaria is listed in Table 1.

TABLE 1

In vitro suppression of *Plasmodium falciparum* when treated with homoharringtonine and chloroquine.

| Strain | Concentration of Homoharringtonine | Concentration of Chloroquine |
|---|---|---|
| Smith/Vietnam | 1.48 ± 0.02 ng/ml (2.7 nM) | 70.0 ng/ml (219 nM) |
| Camp/Malay | 1.36 ± 0.02 ng/ml (2.5 nM) | 6.12 ng/ml (19 nM) |
| FCR-3/Gambia | 1.88 ± 0.02 ng/ml (3.4 nM) | 10.25 ng/ml (32 nM) |

To convert chloroquine dosages from ng/ml to nM divide by 0.320 to convert homoharringtonine dosages from ng/ml to nM divide by 0.5456.

Pathologically, L1210 tumor cells in culture exposed to homoharringtonine demonstrated karyorrhexis of nuclear constituents. Similar morphological changes were seen on blood film of *Plasmodium falciparum* infected red cell cultures exposed to homoharringtonine.

Homoharringtonine acts by inhibiting protein and nucleic acid synthesis of both DNA and RNA in tumor cells. It is thought to block peptide bond formation and aminoacyl-tRNA binding. It is somewhat cell-cycle specific, with the most marked action on cells in $G_1$ and $G_2$ in monolayer cell cultures of synchronized human oral epidermoid carcinoma cells and human cervical carcinoma cells as well as murine fibroblast cells. However, radiolabeled thymidine studies of tumors in vivo show it is a cell cycle nonspecific agent.

Figure 2:
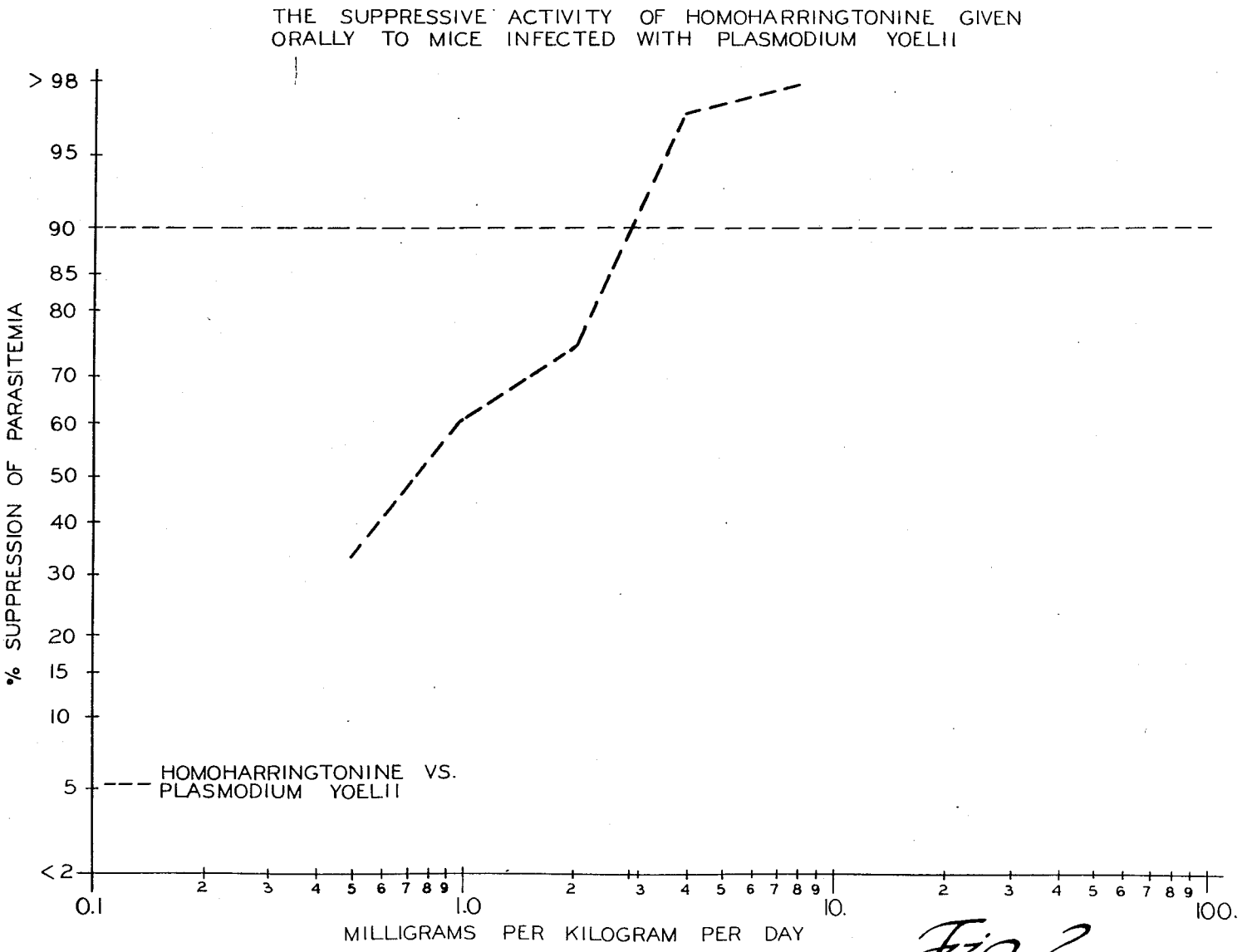

Tests in vivo with malaria-infected mice showed homoharringtoninine to be effective in treating malaria. Mice were divided into sixteen groups of seven mice each and inoculated with $2.5\times10^5$ sporozoites of *Plasmodium yoelii* parasites intraperitoneally. Homoharringtonine was administered twice a day orally and subcutaneously in a volume of 10 ml/kg on the third, fourth and fifth days after inoculation of parasites. The homoharringtonine was mixed in aqueous 0.5% hydroxyethyl cellulose—0.1% Tween-80 and ultrasonicated when necessary. The doses were prepared using 100% free base of the drug. Groups 8 and 16 of the infected mice received the vehicle alone and served as a negative control. The blood films and final group weights were taken on the sixth day after inoculation of parasites. Microscope examination of Giensa-stained blood smears was made to determine the percent parasitemia (percentage of cells parasitized), and percent suppression of parasitemia. The percent suppression of parasitemia is determined by comparing the average parasitemia of the surviving mice with the parasitemia of the negative controls. Toxicity is attributed to drug action when a 14% or greater weight change occurs or when one or more mice die before the blood smears are taken. The results of the in vivo test are shown in Tables 2 and 3 and graphically in FIGS. 1 and 2 for subcutaneous and oral treatments respectively. An effective dosage occurs when the drug produces 90% suppression. This effective dosage for homoharringtonine given subcutaneously is 3.8 mg/kg per day and given orally is 2.8 mg/kg per day.

TABLE 2

In Vivo Suppression of *Plasmodium yoelii* in mice when treated subcutaneously with homoharringtonine.

| Group | Daily Dose (mg/kg) | Total Dosage | % parasitemia of each mouse | Total No. Survivors | Average Parasitemia | % Suppression |
|---|---|---|---|---|---|---|
| 1 | 64.0 | 192.0 | —, —, —, —, —, —, —, | 0 | N.D. | N.D. |
| 2 | 32.0 | 96.0 | —, —, —, —, —, —, —, | 0 | N.D. | N.D. |
| 3 | 16.0 | 48.0 | —, —, —, —, —, —, —, | 0 | N.D. | N.D. |
| 4 | 8.0 | 24.0 | 0.15, 1.0, 0.05, 1.0, 0.25, —, — | 5 | 0.49 | 98.85 |
| 5 | 4.0 | 12.0 | 3.0, 13.0, 4.0, 0.02, 1.0, 0.1, 5.0 | 7 | 3.73 | 91.21 |
| 6 | 2.0 | 6.0 | 16, 40, 20, 13, 5, 28, 23 | 7 | 20.71 | 51.18 |
| 7 | 1.0 | 3.0 | 33, 42, 65, 31, 23, 25, 35 | 7 | 36.29 | 14.48 |
| 8 | Negative Control | | 59, 42, 39, 58, 40, 30, 29 | 7 | 42.43 | |

90% Suppression vs Daily Dose = 3.8 mg/kg

1. — Signifies mouse died toxic death before day 6.

2. N.D. signifies not determined because of toxic death.

TABLE 3

In Vivo suppression of *Plasmodium yoelii* in mice when treated orally with homoharringtonine.

| Group | Daily Dose (mg/kg) | Total Dosage | % Parasitemia For Each Mouse | Total No. Survivors | Average Parasitemia | % Suppression |
|---|---|---|---|---|---|---|
| 9 | 32.0 | 96.0 | —, —, —, —, —, —, —, | 0 | N.D. | N.D. |
| 10 | 16.0 | 48.0 | —, —, —, —, —, —, —, | 0 | N.D. | N.D. |
| 11 | 8.0 | 24.0 | 0.02, 0.01, 0.01 —, —, —, —, | 3 | 0.01 | 99.97 |
| 12 | 4.0 | 12.0 | 0.05, 1.0, 0.25, 0.5, 6.0, 0.25, 0.5 | 7 | 1.22 | 97.55 |
| 13 | 2.0 | 6.0 | 8, 12, 14, 5, 22, 16, 12 | 7 | 12.71 | 74.50 |
| 14 | 1.0 | 3.0 | 13, 10, 15, 35, 31 24, 7 | 7 | 19.29 | 61.32 |
| 15 | 0.5 | 1.5 | 44, 21, 16, 39, 29, 27, 56 | 7 | 33.14 | 33.52 |
| 16 | Negative Control | | 35, 29, 66, 71, 45, 50, 53 | 7 | 49.86 | |

90% Suppression vs Daily Dose = 2.8 mg/kg
1. — Signifies mouse died toxic death before daily 6.
2. N.D. signifies not determined because of toxic death.

The mice studies suggest a daily dosage between 2.8 mg/kg to 3.8 mg/kg. The clinical cancer studies showed safe dosages of 5.0 mg/m$^2$ administered by continuous infusion. An average man has a surface area of about 1.7 m$^2$, therefore, the clinical studies would indicate safe daily doses of 8.5 mg. An average man weighs 80 kg, therefore, the mice studies suggest daily doses of about 224–304 mg per day for a man. But prospective dosages in mice cannot be extrapolated to humans. The physiology is so different as to make any comparisons about dosages worthless. Mice are not susceptible to the human parasite *Plasmodium falciparum* and had to be treated using the mouse parasite *Plasmodium yoelii*. This difference also makes dosage comparisons between mice and humans useless. Homoharringtonine was found to be extremely effective at slowing the parasite's growth in human red cells. Referring to Table 1, homoharringtonine was found to be from 4 to 47 times more effective against malaria infected red cells than the standard antimalaria drug, chloroquine. The increased effectiveness of homoharringtonine should be sufficient for the treatment of malaria in doses safe for humans.

I wish it to be understood that I do not desire to be limited to the exact details of construction shown and described for obvious modifications will occur to a person skilled in the art, without departing from the spirit and scope of the appended claims.

I claim:

1. A method of treating animals for remission of malaria strains of *Plasmodium falciparum* comprising administering to said animals by injecting an amount of an active alkaloid compound, said compound having the following structure:

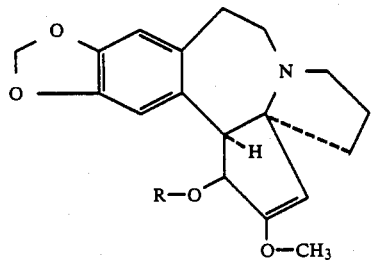

where R is selected from the group consisting of

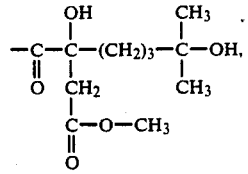

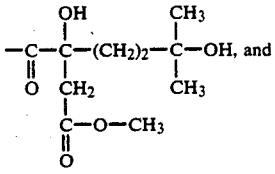

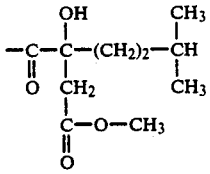

in a dosage effective to cause remission.

2. The method as described in claim 1 wherein R is:

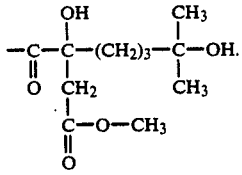

3. The method as described in claim 1 wherein R is:

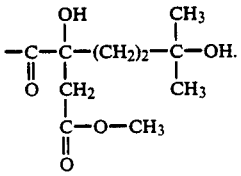

4. The method as described in claim 1 wherein R is:

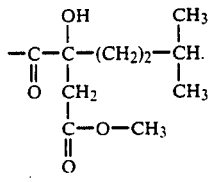

5. The method as described in claim 1 wherein said alkaloid compound is administered by continuous infusion.

6. The method as described in claim 2 wherein 5.0 mg/m$^2$ per day of alkaloid compound is administered by continuous infusion for up to nine days.

7. A method of treating animals for remission of malaria strains of *Plasmodium faciparum* comprising administering to said animals by continuous infusion 0.15–0.30 mg/kg per day up to 10 days repeated after 7 to 14 days of active alkaloid compound having the following structure:

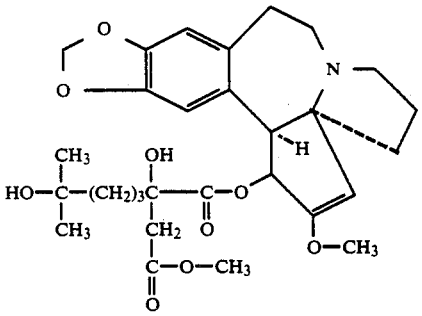

8. A method of treating animals for remission of malaria strains of *Plasmodium yoleii* comprising administering to said animals by injecting an amount of an active alkaloid compound, said compound having the following structure:

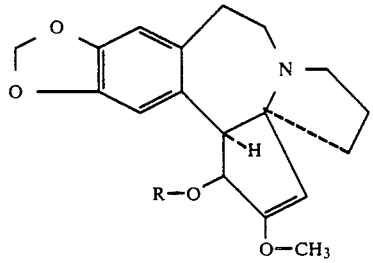

where R is selected from the group consisting of

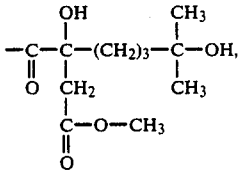

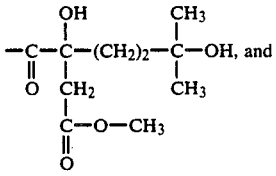

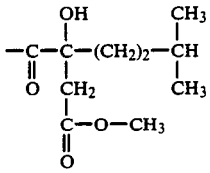

in a dosage effective to cause remission.

9. The method as described in claim 8 wherein R is

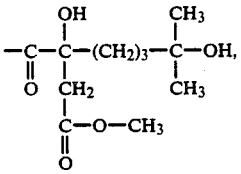

and said alkaloid compound is administered subcurtaneously in daily doses of approximately 3.8 mg/kg for six days.

* * * * *